(12) United States Patent
Lukas et al.

(10) Patent No.: US 6,797,701 B2
(45) Date of Patent: Sep. 28, 2004

(54) ANTIPARASITIC FORMULATIONS

(75) Inventors: Timothy Michael Lukas, Kent (GB); Stephen Richard Wicks, Kent (GB)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 09/978,936

(22) Filed: Oct. 16, 2001

(65) Prior Publication Data
US 2002/0028780 A1 Mar. 7, 2002

Related U.S. Application Data

(63) Continuation of application No. 09/443,279, filed on Nov. 18, 1999, now abandoned.

(30) Foreign Application Priority Data

Nov. 19, 1998 (GB) ............................................. 9825402

(51) Int. Cl.⁷ ................................................. A61K 31/70
(52) U.S. Cl. ............................................ 514/28; 514/27
(58) Field of Search ....................................... 514/28, 27

(56) References Cited

U.S. PATENT DOCUMENTS

| | | | | |
|---|---|---|---|---|
| 3,839,234 A | | 10/1974 | Roscoe | 252/544 |
| 4,206,205 A | | 6/1980 | Mrozik et al. | 424/180 |
| 4,799,522 A | | 1/1989 | Ilon | 152/213 |
| 4,859,499 A | | 8/1989 | Sauvinet et al. | 427/108 |
| 5,945,445 A | * | 8/1999 | Barringer et al. | |
| 6,429,333 B1 | | 8/2002 | Saari et al. | 514/30 |
| 6,482,425 B1 | | 11/2002 | Huet et al. | 424/406 |

FOREIGN PATENT DOCUMENTS

| | | | |
|---|---|---|---|
| EP | 0308145 | 3/1989 | |
| EP | 0379341 | 7/1990 | ........... C07H/17/08 |
| EP | 0214731 | 1/1991 | |
| EP | 0170006 | 4/1992 | |
| EP | 0335541 | 7/1992 | |
| EP | 0317148 | 2/1993 | |
| EP | 0284176 | 8/1993 | |
| EP | 0340832 | 12/1993 | |
| EP | 0350187 | 1/1994 | |
| EP | 0410615 | 1/1994 | |
| EP | 0254583 | 9/1994 | |
| EP | 0334484 | 3/1998 | |
| GB | 1390336 | 4/1975 | |
| GB | 1573955 | 8/1980 | |
| GB | 2095107 | 7/1981 | ........... A61K/47/00 |
| GB | 2189392 | 10/1987 | ............ A61K/7/48 |
| GB | 2334888 | 8/1999 | ........... A01N/47/02 |
| WO | WO 93/07149 | 4/1993 | ......... C07D/487/04 |
| WO | 9415944 | 7/1994 | |
| WO | WO 94/26113 | 11/1994 | ........... A01N/43/90 |
| WO | 9522552 | 8/1995 | |
| WO | WO 97/28126 | 8/1997 | |
| WO | WO 98/11780 | 3/1998 | ........... A01N/47/02 |

OTHER PUBLICATIONS

Fisher, M. and Mrozik, H., *Invermectin and Abamectin*, "Chemistry", Chapter 1: 1–23, WC Campbell, Springer Verlag, NY, 1989.

Chen, S., et al., *Invermectin and Abamectin*, "Biosynthesis", Chapter 4: 55–72, WC Campbell, Springer Verlag, NY, 1989.

Chiu, S.H. and Lu, A., *Invermectic and Abamectin*, Chapter 8(IV, V, VI.): 135–141, WC Campbell, Springer Verlag, NY, 1989.

Goudie, A.C., et al., *Veterinary Parasitology*, "Doramectin—a potent novel endectocide", 49: 5–15, 1993.

* cited by examiner

*Primary Examiner*—Elli Peselev
(74) *Attorney, Agent, or Firm*—Peter C. Richardson; Gregg C. Benson; Raymond D. Thompson

(57) ABSTRACT

A long-acting antiparasitic formulation suitable for topical application including:

(a) 0.1–50% w/v an avermectin or milbemycin having activity against endo- and/or ectoparasites;

(b) 1–50% v/v a di($C_{2-4}$ glycol) mono($C_{1-4}$ alkyl) ether;

(c) an optional antioxidant; and (d) an optional skin acceptable volatile solvent q.s. v/v.

20 Claims, No Drawings

ANTIPARASITIC FORMULATIONS

CROSS REFERENCE TO RELATED APPLICATIONS

This application claims cont. from U.S. patent application No. 09/443,279, filed Nov. 18, 1999 now abandoned and from United Kingdom Application No. 9825402.2, filed Nov. 19, 1998.

FIELD OF INVENTION

This invention relates to antiparasitic formulations, particularly antiparasitic formulations containing avermectins or milbemycins, including derivatives thereof, suitable for topical application to mammals, including humans and domestic animals such as cats and dogs, and which are useful in the treatment of conditions caused by endo- and/or ectoparasites. Especially of interest are formulations of substances active against fleas and/or heartworms.

BACKGROUND OF THE INVENTION

Antiparasitic avermectins, milbemycins and their derivatives have been described in numerous publications, see for example European Patent Applications publication nos. 0 214 731, 0 284 176, 0 317 148, 0 308 145, 0 340 832, 0 335 541, 0 350 187, 0 170 006, 0 254 583, 0 334 484, 0 410 615, British Patent Application numbers 1 573 955, 1 390 336, International Patent Applications publication nos. WO 94/15944 and WO 95/22552, "Ivermectin and Abamectin", W C Campbell, Springer Verlag, New York (1989), and "Doramectin—a potent novel endectocide", A C Goudie et al, Vet.Parasitol. 49 (1993)5.

A number of such substances have been developed for commercialisation, for example ivermectin (Ivomec™), doramectin (Dectomax™), moxidectin and abamectin (Avomec™).

International Patent Application publication no. WO 94/15944, the teaching of which is herein incorporated by reference in its entirety, describes a family of 5-oximino derivatives of avermectin 13-monosaccharides having activity in the treatment of a number of conditions caused by endo- and/or ectoparasites, including 5-oximino22,23-dihydro-25-cyclohexylavermectin B1 monosaccharide (selamectin, Example 5).

We describe herein long-acting formulations suitable for topical application that are capable of delivering avermectins and milbemycins with activity against endo- and/or ectoparasites. These formulations have good cosmetic profiles, stability on storage, cutaneous tolerability, and transdermal delivery characteristics.

SUMMARY OF THE INVENTION

According to one aspect of the invention there is provided a long-acting antiparasitic formulation suitable for topical application including:

(a) about 0.1–50% w/v an avermectin or milbemycin having activity against endo- and/or ectoparasites;
(b) about 1–50% v/v a di($C_{2-4}$ glycol) mono($C_{1-4}$ alkyl) ether;
(c) optional antioxidant; and
(d) an optional skin acceptable volatile solvent q.s. v/v.

DETAILED DESCRIPTION OF THE INVENTION

By "w/v" is meant weight/volume, i.e. "1% w/v" means 1 g in 100 ml of the formulation.

The formulations of the invention have a good cosmetic profile. For instance when applied topically to the fur of a domestic animal such as a cat or dog, they spread well giving good skin contact across a wide range of temperatures. They do not leave an unsightly oily patch, of the type associated with some commercial avernectin or milbemycin formulations in fatty excipients.

Certain of the formulations according to the invention are effective enough to enable long periods, e.g. a several weeks or a month, between treatments.

Preferably the active compound has activity against both endo- and ectoparasites.

Preferably the active compound is selected from ivermectin, doramectin, abamectin, moxidectin, and the avermectin 13-monosaccharide 5-oximes generically and specifically disclosed in International Patent Application publication no. WO 94/15944.

Most preferably the active compound is 5-oximino-22,23-dihydro-25-cyclohexylavermectin B1 monosaccharide (selamectin).

Preferably the di($C_{2-4}$ glycol) mono($C_{1-4}$ alkyl) ether is diethylene glycol monomethyl ether (DEGMME) or dipropylene glycol monomethyl ether (DPGMME).

More preferably the glycol monomethyl ether is DPGMME.

Any source of pharmaceutical/veterinary quality di($C_{2-4}$ glycol) mono($C_{1-4}$ alkyl) ethers may be used. For instance, an acceptable commercial source of DPGMME is Dow Corning, whose product "Dowanol DPM™" has the following characteristics: B.pt. 74.6° C. at 13 mbar, freezing point −83° C., density 0.948 g/cm$^3$ at 25° C., viscosity 3.72 mPas at 25° C. and refractive index of 1.421 at 25° C.

Preferably the di($C_{2-4}$ glycol) mono($C_{1-4}$ alkyl) ether is present in the formulation at a level of up to about 20% v/v, yet more preferably in the range about 2–16% v/v, further more preferably in the range about 4–12% v/v, and most preferably in the range about 6–12% v/v.

Preferably the skin acceptable volatile solvent is present and is ethanol or isopropanol (IPA).

More preferably the skin acceptable solvent is IPA.

Preferably the w/v to v/v ratio of active compound to the glycol monomethyl ether is in the range about (0.5 to 2) to 1.

More preferably the w/v to v/v ratio of active compound to the glycol monomethyl ether is about (0.7 to 1.4) to 1.

Yet more preferably the w/v to v/v ratio of active compound to the glycol monomethyl ether is about (0.9 to 1.1) to 1.

Most preferably the w/v to v/v ratio of active compound to the glycol monomethyl ether is about 1:1.

Preferably the level of active avermectin or milbemycin in the total formulation is in the range about 1% to about 16% w/v, more preferably about 4% to about 12% w/v, yet more preferably about 6 to about 12% w/v.

Optionally the formulation can further include an antioxidant, such as propylgallate, BHA (2-t-butyl-4-methoxyphenol), or BHT (2,6-di-t-butyl-4-methylphenol).

Preferably, the antioxidant, if present, is BHT.

Preferably, the antioxidant, if present, is at a level of less than 0.2% w/v, more preferably less than 0.1% w/v.

Preferably the formulation consists of:

(a) 5-oximino-22,23-dihydro-25-cyclohexylavermectin B1 monosaccharide (selamectin, at a level of 1% to 16% w/v);

(b) DEGMME or DPGMME at 1 to 16% v/v, and at a w/v to v/v ratio of active compound to DEGMME/DPGMME of about 1:1;
(c) isopropanol q.s. 100% v/v;
and, optionally (d) BHT (at less than 0.1% w/v).

More preferably the formulation consists of:
(a) 5-oximino-22,23-dihydro-25-cyclohexylavermectin B1 monosaccharide (selamectin, at a level of 6% to 12% w/v);
(b) DEGMME or DPGMME 6 to 12% v/v, and at a w/v to v/v ratio of active compound to or DEGMME/DPGMME of about 1:1;
(c) isopropanol q.s. 100% v/v;
and, optionally (d) BHT (at less than 0.1% w/v).

A preferred group of formulations consists of the formulations mentioned in the Examples below.

Another aspect of the invention is a method of treatment of a condition caused by an endo- or ectoparasite by administration of an effective amount of a formulation according to the invention.

Another aspect of the invention is a formulation according to the invention for use in medicine.

Another aspect of the invention is the use of a formulation according to the invention in the manufacture of a medicament for the treatment of conditions caused by endo- and/or ecto-parasites.

Formulations according to the invention can be made by standard methods, for example by dissolution of the avermectin and/or milbemycin and optional antioxidant in the solvent or solvents, in accordance with standard pharmaceutical or veterinary practice, e.g. by agitation of a mixture of the ingredients, if necessary with concurrent warming.

The amount of antiparasitic avermectin/milbemycin material in a unit dose of the formulation can of course vary depending on the efficacy of the avermectin/milbemycin in treating the condition of interest, the desired frequency of application, etc., according to standard veterinary and pharmaceutical practice.

The formulations of the invention can be administered in a way appropriate to the specific use envisaged, the particular species and weight of host animal being treated, the parasite or parasites involved, degree of infestation, etc., according to standard medical and veterinary practice.

For example, for dogs and cats, a dose of 5-oximino-22,23-dihydro-25-cyclohexylavermectin B1 monosaccharide (selamectin) of between 4 mg/kg and 12 mg/kg, preferably about 9 mg/kg body weight of the host animal as a single dose once per month will be satisfactory for flea control and heartworm prophylaxis, but of course there will be instances where higher or lower dosage ranges are indicated and such are within the scope of this invention. A typical dosage regime for a 6 mg/kg dose, to a domestic animal such as a typical domestic cat or dog, would be 0.25 ml to 2 ml of the formulation of Example 1 per dose per month.

The formulations according to the invention are especially suitable to be administered topically. For topical application, dip, spray, pour-on, spot-on, jetting fluid, shampoos, collar, tag or harness may be used. Particularly preferred is a spot-on formulation.

It is to be understood that reference to treatment indudes prevention, alleviation and cure of the condition or conditions caused by the parasite or parasites.

The invention is illustrated by the following examples, in which
(i) the BHT antioxidant (if present) was dissolved in a mixture of DPGMME or DEGMME and IPA,
(ii) the drug substance was added, and the mixture stirred until dissolution took place,
(iii) any residue was filtered off prior to filling into appropriate containers.

EXAMPLE 1

A formulation consisting of
(a) 5-oximino-22,23-dihydro-25-cyclohexylavermectin B1 monosaccharide at 6% w/v
(b) DPGMME at 6% v/v
(c) BHT at 0.08% w/v
(d) IPA q.s. 100% v/v.

EXAMPLE 2

A formulation consisting of
(a) 5-oximino-22,23-dihydro-25-cyclohexylavermectin B1 monosaccharide at 6% w/v
(b) DPGMME at 6% v/v
(c) IPA q.s. 100% v/v.

EXAMPLE 3

A formulation consisting of
(a) 5-oximino-22,23-dihydro-25-cyclohexylavermectin B1 monosaccharide at 8% w/v
(b) DPGMME at 16% v/v
(c) BHA 0.1% w/v
(d) IPA q.s. 100% v/v.

EXAMPLE 4

A formulation consisting of
(a) 5-oximino-22,23-dihydro-25-cyclohexylavermectin B1 monosaccharide at 12% w/v
(b) DPGMME at 12% v/v
(c) BHT at 0.08% w/v
(d) IPA q.s. 100% v/v.

EXAMPLE 5

A formulation consisting of
(a) 5-oximino-22,23-dihydro-25-cyclohexylavermectin B1 monosaccharide at 12% w/v
(b) DPGMME at 12% v/v
(c) IPA q.s. 100% v/v.

EXAMPLE 6

A formulation consisting of
(a) 5-oximino-22,23-dihydro-25cyclohexylavermectin B1 monosaccharide at 16% w/v
(b) DPGMME at 16% v/v
(c) BHA 0.1% w/v
(d) IPA q.s. 100% v/v.

EXAMPLE 7

A formulation consisting of
(a) 5-oximino-22,23-dihydro-25-cyclohexylavermectin B1 monosaccharide at 16% w/v
(b) DEGMME at 16% v/v
(c) IPA q.s. 100% v/v.

EXAMPLE 8

A formulation consisting of
(a) 5-oximino-22,23-dihydro-25-cyclohexylavermectin B1 monosaccharide at 16% w/v
(b) DPGMME at 8% v/v
(c) IPA q.s. 100% v/v.

EXAMPLE 9

A formulation consisting of
(a) 5-oximino-22,23-dihydro-25-cyclohexylavermectin B1 monosaccharide at 16% w/v
(b) DPGMME at 16% v/v
(c) IPA q.s. 100% v/v.

EXAMPLE 10

A formulation consisting of
(a) 5-oximino-22,23-dihydro-25-cyclohexylavermectin B1 monosaccharide at 16% w/v
(b) DEGMME at 8% v/v
(c) IPA q.s. 100% v/v.

EXAMPLE 11

A formulation with the following ingredients (in mg/ml):
(a) 5-oximino-22,23-dihydro-25-cyclohexylavermectin B1 monosaccharide (60);
(b) DPGMME (56.28);
(c) BHT (0.8); and
(d) IPA (697.92).

EXAMPLE 12

A formulation with the following ingredients (in mg/ml):
(a) 5-oximino-22,23-dihydro-25-cyclohexylavermectin B1 monosaccharide (120);
(b) DPGMME (112.56);
(c) BHT (0.8); and
(d) IPA (613.64).

EXAMPLE 13

The efficacy of the formulations according to the invention is illustrated by the following. Three formulations of selamectin were administered as a single topical dose of 8 mg/kg, and evaluated over time against induced infestations of the flea (Ctenocephalides felis) on dogs. The three formulations each contained 160 mg/mL of selamectin and, respectively, 16% w/v diethylene glycol monomethyl ether (DEGMME), 8% w/v dipropylene glycol monomethyl ether (DPGMME) or 16% w/v DPGMME, with isopropanol to volume. Thirty-six dogs (16 males and 20 females) previously infested with 100 unfed viable adult fleas were allocated randomly by flea count to one of four groups which subsequently received saline (negative control, T1), selamectin in 16% w/v DEGMME (T2), selamectin in 8% w/v DPGMME (T3), and selamectin in 16% w/v DPGMME (T4). Treatment was administered topically at the base of the neck in front of the shoulder blades on day 0. Efficacy was assessed by comb counts of viable fleas present on each dog. Each dog was infested with approximately 100 unfed viable adult C. felis on days 1, 4. 11, 18, 23, 27, 32, and 39, and comb counts were conducted approximately 72 hours after each infestation, on days 4, 7, 14, 21, 26, 30, 35 and 42. There were no adverse drug reactions and no mortalities during the study. Geometric mean flea comb counts for each of the three selamectin formulations were significantly lower ($Ps \leq 0.05$) than those of the saline control on each post-treatment flea counting day. Efficacies (percentage reductions in geometric mean flea comb counts) on day30 were 98.6%, 98.2% and 99.4% for T2, T3 and T4, respectively. On day 35, efficacies for T2, T3 and T4 were 93.5%, 95.9% and 97.7%, respectively. Efficacies on day 42 were 67.3%, 82.3% and 88.1% for T2, T3, and T4, respectively.

The efficacy of a selamectin formulation, administered topically at dosages of 3 mg/kg, 6 mg/kg and 9 mg/kg, was evaluated against induced infestations of Ctenocephalides felis on dogs for the determination of an appropriate dose. The formulation contained 12% (120 mg/mL) of selamectin and 11.26% w/v dipropylene glycol monomethyl ether (DPGMME) in isopropanol. Forty-eight dogs (24 males and 24 females) were allocated randomly by flea counts within sex to one of four groups: placebo (negative control, T1) or selamectin at 3 mg/kg (T2), 6 mg/kg (T3 ) or 9 mg/kg (T4 ). On day 0, treatments were administered topically on the animal's back at the base of the neck in front of the shoulder blades. Efficacy was assessed by comb counts of live fleas present on each dog. Each dog was infested with approximately 100 unfed viable adult C. felis on days 4, 11, 18 and 27, and comb counts were conducted approximately 72 hours after each infestation, on days 7, 14, 21 and 30, respectively. There were no adverse drug reactions and no mortalities during the study. Percentage reductions in geometric mean flea comb counts for the three selamectin treatments ranged from 94.6% to 100% on days 7, 14 and 21. On day 30, percentage reductions were 81.5%, 94.7%, and 90.8% for T2, T3, and T4, respectively. Analysis of variance showed that day 30 flea comb counts for the treated groups (T2, T3 and T4 combined) were significantly lower ($P \leq 0.05$) than for placebo (T1), and that counts for the 3 mg/kg treatment (T2 ) were significantly higher ($P \leq 0.05$) than for the 6 mg/kg and 9 mg/kg treatments (T3 and T4 combined), which were not statistically different ($P > 0.10$).

What is claimed is:

1. An antiparasitic formulation consisting essentially of:
    (a) about 0.1–50% w/v of an avermectin 13-monosaccharide 5-oxime having activity against an endoparasite or ectoparasite or both;
    (b) about 1–50% v/v of a di($C_{2-4}$ glycol)mono($C_{1-4}$ alkyl) ether;
    (c) an optional antioxidant; and
    (d) an optional skin acceptable volatile solvent q.s. v/v.
2. A formulation according to claim 1 wherein said v/v of said di($C_{2-4}$ glycol)mono($C_{1-4}$ alkyl)ether is about 1-20%.
3. A formulation according to claim 1 wherein said avermectin 13-monosaccharide 5-oxime has activity against both endo- and ectoparasites.
4. A formulation according to claim 1 wherein said avermectin 13-monosaccharide 5-oxime is 5-oximino-22,23-dihydro-25-cyclohexylavermectin B1 monosaccharide.
5. A formulation according to claim 1 wherein said di($C_{2-4}$ glycol)mono($C_{1-4}$ alkyl) ether is diethylene glycol monomethyl ether (DEGMME) or dipropylene glycol monomethyl ether (DPGMME).
6. A formulation according to claim 5 wherein said di($C_{2-4}$ glycol)mono($C_{1-4}$ alkyl) ether is dipropylene glycol monomethyl ether (DPGMME).
7. A formulation according to claim 1 wherein the skin-acceptable solvent is present and is ethanol or isopropanol.
8. A formulation according to claim 7 wherein the skin-acceptable solvent is isopropanol.

9. A formulation according to claim 1 wherein the ratio of said % w/v of an avermectin 13-monosaccharide 5-oxime to said % v/v of a di($C_{2-4}$ glycol)mono($C_{1-4}$ alkyl) ether is about (0.5 to 2) to 1.

10. A formulation according to claim 1 wherein the ratio of said % w/v of an avermectin 13-monosaccharide 5-oxime to said % v/v of a di($C_{2-4}$ glycol)mono($C_{1-4}$ alkyl) ether is about (0.7 to 1.4) to 1.

11. A formulation according to claim 1 wherein the ratio of said % w/v of an avermectin 13-monosaccharide 5-oxime to said % v/v of a di($C_{2-4}$ glycol)mono($C_{1-4}$ alkyl) ether is (0.9 to 1.1) to 1.

12. A formulation according to claim 1 wherein the ratio of said % w/v of an avermectin 13-monosaccharide 5-oxime to said % v/v of a di($C_{2-4}$ glycol)mono($C_{1-4}$ alkyl) ether is about 1:1.

13. A formulation according to claim 1 wherein said % w/v of an avermectin 13-monosaccharide 5-oxime in the total formulation ranges from about 1% to about 16%.

14. A formulation according to claim 13 wherein said % w/v of an avermectin 13-monosaccharide 5-oxime in the total formulation ranges from about 4% to about 12%.

15. An antiparasitic formulation comprising:
(a) about 6% to about 12% of an avermectin 13-monosaccharide 5-oxime having activity against an endoparasite or ectoparasite or both;
(b) about 1-50% v/v of a di($C_{2-4}$ glycol)mono($C_{1-4}$ alkyl) ether;
(c) an optional antioxidant; and
(d) an optional skin acceptable volatile solvent q.s. v/v.

16. A formulation according to claim 1 wherein said antioxidant is present, and is selected from the group consisting of: propylgallate, 2-t-butyl-4-methoxyphenol (BHA), and 2,6-di-t-butyl-4-methylphenol (BHT).

17. formulation according to claim 16 wherein said antioxidant is 2,6-di-t-butyl-4-methylphenol (BHT).

18. An antiparasitic formulation consisting essentially of:
(a) about 1% to 16% w/v of 5-oximino-22,23-dihydro-25-cyclohexylavermectin B1 monosaccharide;
(b) about 1 to 16% v/v of diethylene glycol monomethyl ether (DEGMME) or dipropylene glycol monomethyl ether (DPGMME); wherein the ratio of said % w/v of 5-oximino-22,23-dihydro-25-cyclohexylavermectin B1 monosaccharide to said % v/v of diethylene glycol monomethyl ether (DEGMME) or dipropylene glycol monomethyl ether (DPGMME) is about 1:1;
(c) isopropanol q.s. 100% v/v;
and, optionally (d) less than about 0.1% w/v of 2,6-di-t-butyl-4-methylphenol (BHT).

19. An antiparasitic formulation which comprises:
(a) about 6% to 12% w/v of 5-oximino-22,23-dihydro-25-cyclohexylavermectin B1 monosaccharide;
(b) about 6 to 12% v/v of diethylene glycol monomethyl ether (DEGMME) or dipropylene glycol monomethyl ether (DPGMME).
(c) isopropanol q.s. 100% v/v; and, optionally (d) less than about 0.1% w/v of 2,6-di-t-butyl-4-methylphenol (BHT).

20. A method of treating a condition in a mammal caused by an endoparasite or ectoparasite or both which comprises topical administration of an effective amount of a formulation according to one of claims 1–3 and 5–19 to the mammal suffering from the condition.

* * * * *

UNITED STATES PATENT AND TRADEMARK OFFICE
CERTIFICATE OF CORRECTION

| | | |
|---|---|---|
| PATENT NO. | : 6,797,701 B2 | Page 1 of 1 |
| APPLICATION NO. | : 09/978936 | |
| DATED | : September 28, 2004 | |
| INVENTOR(S) | : Timothy Michael Lukas et al. | |

It is certified that error appears in the above-identified patent and that said Letters Patent is hereby corrected as shown below:

In the Claims

Column 8, claim 20, line 32 should read: "tion according to one of claims 1-19 to the mammal".

Signed and Sealed this
Seventh Day of October, 2014

Michelle K. Lee
*Deputy Director of the United States Patent and Trademark Office*